United States Patent
Graham (10) Patent No.: US 8,833,606 B2
(45) Date of Patent: Sep. 16, 2014

(54) DEVICE AND METHOD FOR MIXING AND APPLYING BIOMATERIALS

(75) Inventor: Marc Miller Graham, Sommerville, MA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 86 days.

(21) Appl. No.: 13/342,703

(22) Filed: Jan. 3, 2012

(65) Prior Publication Data

US 2013/0168409 A1 Jul. 4, 2013

(51) Int. Cl.
B67B 7/00 (2006.01)

(52) U.S. Cl.
USPC .............. 222/1; 222/80; 222/145.6; 222/229; 222/235; 604/88; 206/219; 206/229; 366/204; 366/286

(58) Field of Classification Search
USPC .............. 604/82–92; 206/219, 221, 229–230; 366/187–188, 197–207, 285–286; 222/1, 80–91, 145.1, 145.5–145.6, 222/229, 235, 333
See application file for complete search history.

(56) References Cited

U.S. PATENT DOCUMENTS

| | | | |
|---|---|---|---|
| 2,588,629 A | 3/1952 | Hull | |
| 2,708,438 A | 5/1955 | Cohen | |
| 2,709,989 A | 6/1955 | Mansheim | |
| 2,775,228 A | 12/1956 | Smith | |
| 2,783,741 A | 3/1957 | Maczynski | |
| 2,898,885 A | 8/1959 | Hansen | |
| 3,004,520 A | 10/1961 | Kersten et al. | |
| 3,051,131 A | 8/1962 | Schwarzäugl | |
| 3,191,329 A | 6/1965 | Shea | |
| 3,195,778 A | 7/1965 | Coates | |
| 3,228,378 A * | 1/1966 | Rohrmuller | 401/109 |
| 3,288,115 A | 11/1966 | Hechtle | |
| 3,341,962 A | 9/1967 | Siegel | |
| 3,373,906 A * | 3/1968 | De Hart et al. | 222/235 |
| 3,756,390 A | 9/1973 | Abbey et al. | |
| 3,881,484 A * | 5/1975 | Gidcumb, Jr. | 604/89 |
| 4,116,240 A | 9/1978 | Guiney | |
| 4,193,698 A * | 3/1980 | Gartner | 366/130 |
| 4,221,290 A * | 9/1980 | Bast | 206/219 |
| 4,277,184 A * | 7/1981 | Solomon | 366/139 |
| 4,556,325 A * | 12/1985 | Katzin | 366/130 |
| 4,991,988 A * | 2/1991 | Snell et al. | 401/111 |
| 5,273,190 A | 12/1993 | Lund | |
| 5,630,800 A | 5/1997 | Blank et al. | |
| 5,842,786 A * | 12/1998 | Solomon | 366/139 |
| 6,367,962 B1 | 4/2002 | Mizutani et al. | |
| 6,550,957 B2 | 4/2003 | Mizutani et al. | |

(Continued)

Primary Examiner — Paul R Durand
Assistant Examiner — Andrew P Bainbridge
(74) Attorney, Agent, or Firm — McCracken & Frank LLC (57) ABSTRACT

A device for mixing and applying a substance includes a syringe barrel, a plunger, a shaft, a mixing surface, and a locking device. The syringe barrel is preloaded with one or more components of the substance and is enclosed by a seal. The plunger has a plunger body that is displaceable within the syringe barrel, and a dispensing surface. The shaft within the plunger body has a first end and a second end, and is positioned to extend through and from the plunger body. The mixing surface is attached to the first end of the shaft. The locking device enables the mixing surface to alternate between an extended position and a retracted position. In the extended position, the mixing surface projects from the dispensing surface to promote mixing of the substance. In the retracted position, the mixing surface is retracted through the dispensing surface into the plunger body.

1 Claim, 6 Drawing Sheets

(56) References Cited

U.S. PATENT DOCUMENTS

| | | |
|---|---|---|
| 7,018,089 B2 * | 3/2006 | Wenz et al. ............ 366/130 |
| 7,168,847 B2 | 1/2007 | Frei et al. |
| 7,216,761 B2 | 5/2007 | de Vries |
| 7,469,608 B2 * | 12/2008 | Sekizawa et al. ........ 73/866 |
| 7,905,654 B1 | 3/2011 | Cordero |
| 7,938,572 B2 * | 5/2011 | Lidgren et al. ......... 366/108 |
| 2006/0256646 A1 * | 11/2006 | Bidoia ................... 366/139 |
| 2010/0121310 A1 | 5/2010 | Simonton et al. |
| 2011/0004156 A1 | 1/2011 | Keller |

* cited by examiner

DEVICE AND METHOD FOR MIXING AND APPLYING BIOMATERIALS

CROSS REFERENCE TO RELATED APPLICATIONS

Not applicable.

REFERENCE REGARDING FEDERALLY SPONSORED RESEARCH OR DEVELOPMENT

Not applicable

SEQUENTIAL LISTING

Not applicable

BACKGROUND OF THE DISCLOSURE

1. Field of the Disclosure

The present invention relates to a device and method for mixing and applying biomaterials. More particularly, it pertains to a device comprising a plunger, a mixing surface, and a retractor locking assembly assembled such that the mixing surface can be locked into an extended or a retracted position, and a method wherein the mixing surface is locked in the extended position to mix the biomaterials and locked in the retracted position to apply the biomaterials.

2. Description of the Background of the Disclosure

Bone fillers and cements are widely used in the medical field. Such cements are made by mixing a liquid and powdered component to form a paste which then sets to form a hard cement or filler. These pastes may be placed in situ prior to setting in situations where a bone has been broken, destroyed, degraded, or become too brittle, or as a suture anchor used to attach soft tissue to bone. Rapid setting bone cement compositions are advantageous due to the shortened time required for surgery and recovery after surgery.

One such bone cement is disclosed in U.S. Publication 2010/0121459 to Garigapati comprising tetracalcium phosphate, phosphoserine, and an aqueous medium. Another bone cement disclosed in U.S. Publication 2011/0277931 to Garigapati includes a reactive mixture of a small amino acid phosphate species, a multivalent metal compound, and a polymeric material in an aqueous environment. The multivalent metal compound may be a calcium phosphate, or, more specifically, a tetracalcium phosphate. The small amino acid phosphate species may be phosphoserine or a compound with a similar structure. The bone cement disclosed in U.S. Ser. No. 61/558,214 comprises a non-covalently bonded macromolecular network comprising of a reactive mixture of a small amino acid phosphate species and a bioactive glass material in an aqueous environment. Similar bone cements are further disclosed in U.S. Ser. No. 61/486,064 and U.S. Publication No. 2009/0110743.

In these compositions, the powder component, which includes the calcium phosphate, is supplied in a bottle. The liquid, which includes the phosphoserine or phosphoserine-like substance and optionally other additives such as a polymer or bioactive glass material, is provided in a glass container. The components are usually mixed in a mixing container and transferred to a vessel such as a syringe to be dispensed.

An assembly for mixing a powdered copolymer and a liquid monomer to form a bone cement and delivering the bone cement is disclosed in U.S. Pat. No. 6,547,432 to Coffeen et al. The device comprises a cartridge having a distal end and a proximal end, defining a mixing chamber and having a mixing blade therein. A transfer mechanism supporting a piston and a plunger is connected to the distal end to dispense the bone cement from the proximal end. The device further comprises a removable handle for insertion through the proximal end and attachment to the mixing blade by a quick-release connector. After removal of the handle, the mixing blade remains in the mixing chamber as the bone cement is dispensed from the proximal end.

Another assembly for mixing and delivery is described in U.S. Pat. No. 7,658,537 to Coffeen et al. The device includes a mixer connected to a delivery device by a transfer conduit. Separate components are mixed in the mixer and then automatically transferred through the transfer conduit to the delivery device for delivery of the mixture to the target site.

A further assembly for storing, mixing, and dispensing components disclosed in U.S. Pat. No. 7,736,049 to Keller consists of a first container for a powdery material, a second container for a liquid material, a piston assembly for transferring the liquid component to the first container, a mixing arrangement for mixing the powdery and the liquid components in the first container, and a piston assembly for dispensing the mixed materials. The assembly further comprises a transfer area between the outlet of the second container and the inlet of the first container.

Problems arise when preparing to dispense a bone cement composition onto a host area using a syringe. Additional time is needed to transfer the cement composition from a mixing container into the syringe, or, for the assemblies described above, to attach and detach various parts. Further, such transfer requires the use of both hands. It is therefore necessary to provide a device for mixing and applying biomaterials designed to allow the substance to be mixed and applied from the same vessel, where the device can be locked in either an extended position in order to mix the substance or in a retracted position in order to apply the substance. Further, it is ideal to provide a device that can be rotated relative to the vessel upon movement of the vessel in a circular motion.

SUMMARY OF THE DISCLOSURE

One aspect of the present invention relates to a device and method for mixing and applying biomaterials comprising a plunger having a plunger body and a dispensing surface, wherein the plunger body is displaceable within the syringe barrel, a shaft within the plunger body having a first end and a second end, wherein the shaft is positioned to extend through and from the plunger body, a mixing surface attached to the first end of the shaft, and a locking device that enables the mixing surface to alternate between an extended position and a retracted position. The mixing surface projects from the dispensing surface in the extended position to promote mixing of the substance, and is retracted through the dispensing surface into the plunger body in the retracted position such the dispensing surface may act on and dispense the substance.

Another aspect of the present invention relates to a method for mixing and applying a substance comprising the steps of positioning a mixing surface in an extended position wherein the mixing surface projects from a dispensing surface of a plunger body, positioning the mixing surface and the dispensing surface within a vessel, causing the mixing surface to rotate relative to the vessel, positioning the mixing surface in a retracted position wherein the mixing surface is retracted into the plunger body, and forcing the dispensing surface to act on and dispense the substance.

A further aspect of the invention relates to a kit for applying a bone cement to a surface comprising a vessel and a device for mixing and applying biomaterials. The device comprises a plunger having a plunger body and a dispensing surface, wherein the plunger body is displaceable within the syringe barrel, a shaft within the plunger body having a first end and a second end, wherein the shaft is positioned to extend through and from the plunger body, a mixing surface attached to the first end of the shaft, and a locking device that enables the mixing surface to alternate between an extended position and a retracted position. The mixing surface projects from the dispensing surface in the extended position to promote mixing of the substance, and is retracted through the dispensing surface into the plunger body in the retracted position such the dispensing surface may act on and dispense the substance.

Other aspects and advantages of the present invention will become apparent upon consideration of the following detailed description.

DETAILED DESCRIPTION

Figure 1:
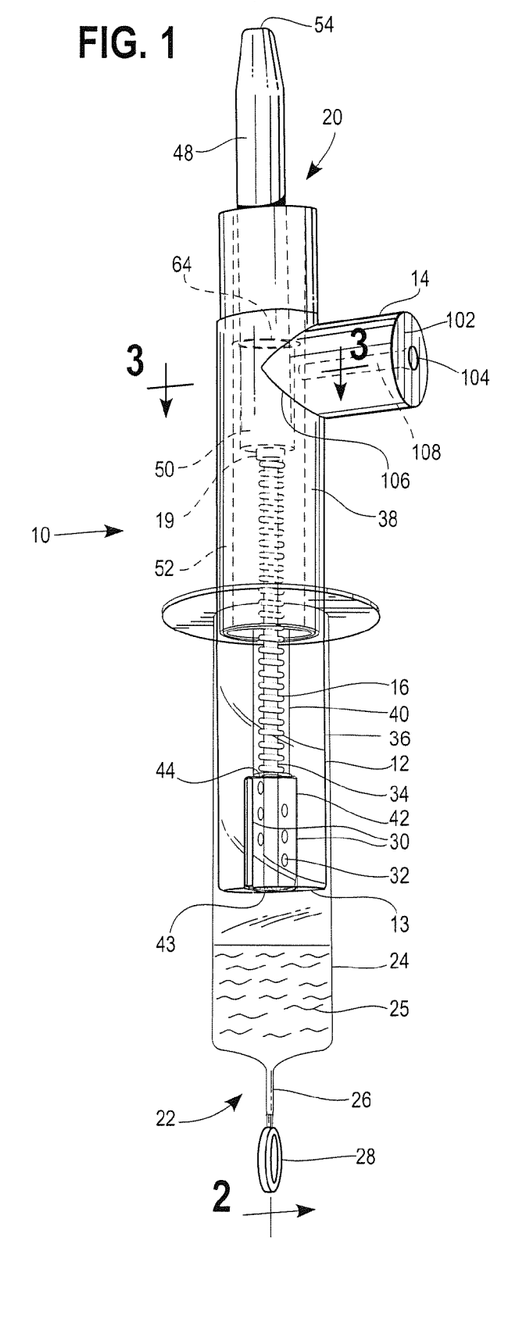
FIG. 1 is a perspective view of the device in the retracted position.
Figure 4:
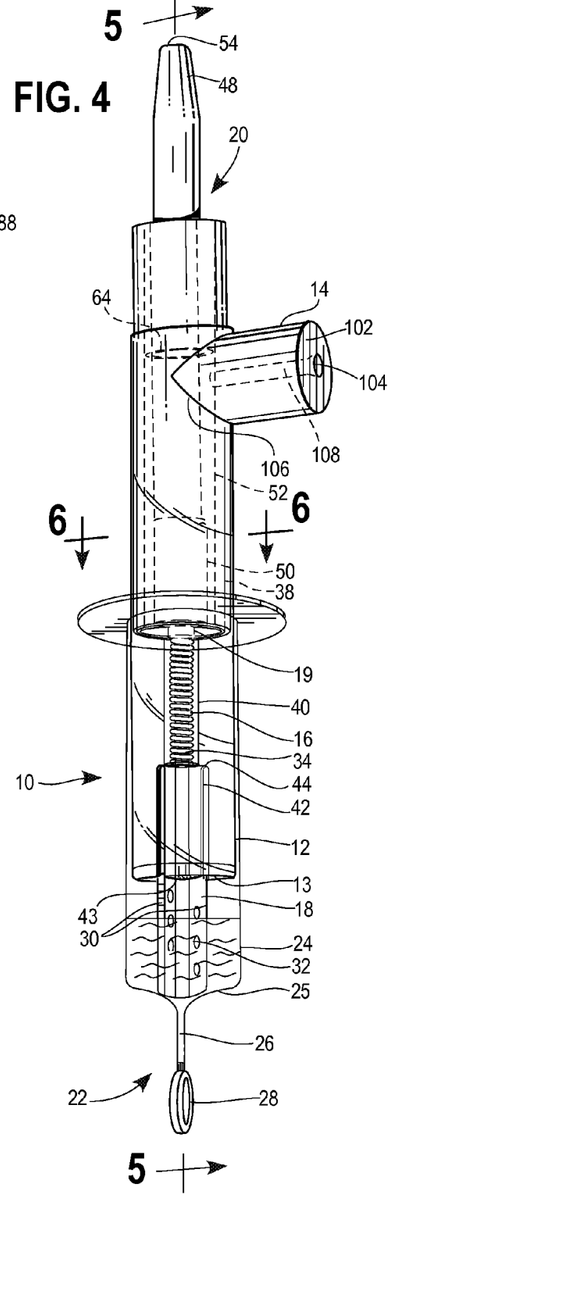
FIG. 4 is a perspective view of the device in the extended position.

With reference to the figures, the device 10 comprises a plunger body 12 having a dispensing surface 13 and an off center mass 14, a shaft 16 having a mixing surface 18 and a shaft cap 19, and a retractor locking assembly 20 adjacent the shaft 16 and shaft cap 19. The retractor locking assembly 20 alternately maintains the mixing surface 18 in a retracted position, wherein the mixing surface 18 is withdrawn into the plunger body 12 as shown in FIG. 1, or an extended position, wherein the mixing surface 18 projects from the dispensing surface 13 the plunger body 12 as shown in FIG. 4. During operation, the device 10 is first locked in the extended position. A user inserts the dispensing surface 13 of plunger body 12 into a syringe 22 containing a substance 25 as seen in FIG. 4. To mix the biomaterials, the user holds the syringe 22 upright with the retractor locking assembly 20 at the highest point and moves the syringe 22 in a circular motion with a small diameter whereby the off center mass 14 causes the device 10 to rotate relative to the syringe 22. When the biomaterials are sufficiently mixed, the user stops the circular motion and actuates the retractor locking assembly 20 to lock the mixing surface 18 in the retracted position as seen in FIG. 1. To apply the biomaterials, the user then positions the syringe 22 over the area to receive the mixed substance 25 and pushes the plunger body 12 into the syringe 22 in order to force the dispensing surface 13 to act on and dispense the substance 25.

As shown in FIGS. 1 and 4, the syringe 22 includes a barrel 24 which may be formed from any suitable plastic material, glass, or similar material. The barrel 24 is preferably transparent or translucent but can be opaque. The barrel 24 has an exit port or nozzle 26 formed at one end which is adapted to receive a protective cap 28 to prevent leakage of the substance from the barrel 24 during mixing. At another end, the barrel 24 is open in order to receive the device 10. The barrel 24 and plunger body 12 are sized such that the plunger body 12 is displaceable within the barrel 24. As described in greater detail below, the substance 25 may be loaded into the barrel 24 immediately before use or may be pre-loaded. While a syringe is shown in FIGS. 1-6, other vessels sized to receive the device 10 may be used.

With reference to FIG. 1, a first end of the shaft 16 extends through the dispensing surface 13 of the plunger body 12 and a second end of the shaft 16 abuts the retractor locking assembly 20. The mixing surface 18 having two edges 30 is secured to the first end of the shaft 16 with at least one screw (not shown) and is projected from the dispensing surface 13 the plunger body 12 in the extended position. The mixing surface 18 extends the full inner diameter of the barrel 24 such that the edges 30 of the mixing surface 18 touch the inner surface of the barrel 24. A plurality of holes 32 is formed on the mixing surface 18 to promote mixing during operation. The shaft cap 19 has an inner diameter that is approximately the same as the outer diameter of the shaft 16 such that the shaft cap 19 is securely held in place on the end of the shaft 16. In the preferred embodiment, a helical spring 34 positioned on the shaft 16 and compressed between a shoulder 44 in the plunger body 12 and the shaft cap 19 continuously urges the device 10 into the retracted position by forcing the shaft 16 and shaft cap 19 toward the retractor locking assembly 20. Alternatively, the shaft 16 may be connected to the retractor locking assembly 20 with the spring 34 compressed between the shoulder 44 in the plunger body 12 and the retractor locking assembly 20.

Figure 2:
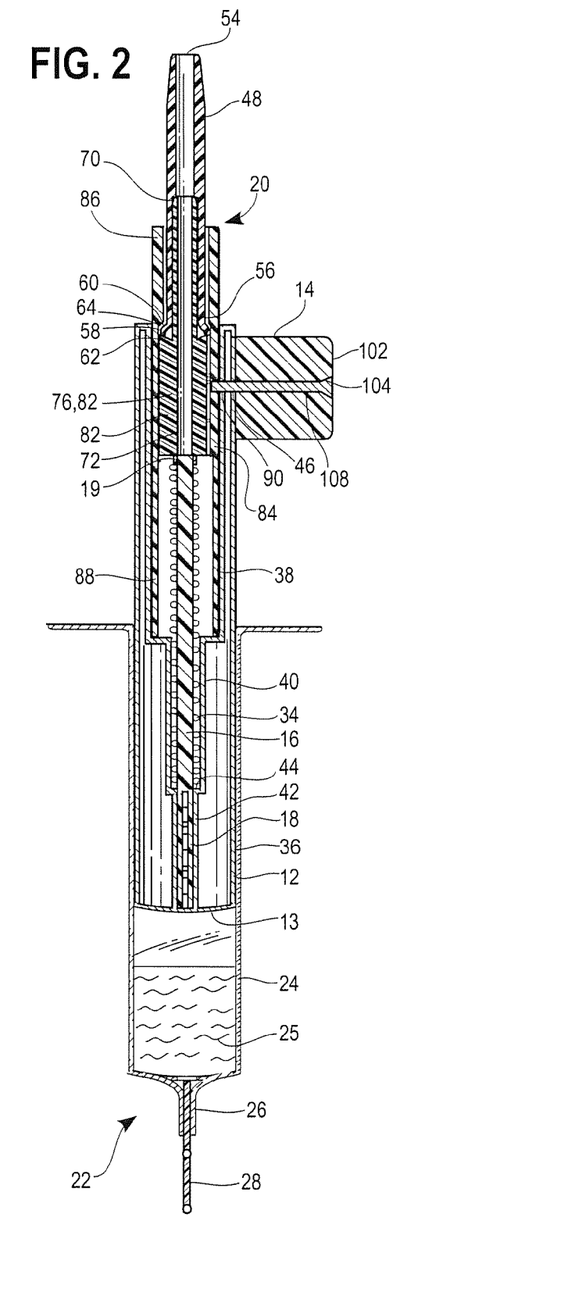
FIG. 2 is a cross sectional view of Section 2-2 of FIG. 1.

Referring to FIGS. 1 and 2, the plunger body 12 having a cylindrical exterior 36 is displaceable within the syringe 22 such that movement of the dispensing surface 13 toward the nozzle 26 acts on and dispenses the substance 25 from the syringe 22. The plunger body 12 includes a first interior portion 38, a second interior portion 40, and a third interior portion 42, wherein the shaft 16 is reciprocatably moveable therein. The plunger body 12 also includes a plunger aperture 46 located near the retractor locking assembly 20 for attachment of the off center mass 14 as described below.

The first interior portion 38 having a hollow cylindrical shape is sized to house the retractor locking assembly 20. The second interior portion 40 having a hollow cylindrical shape is sized to house the shaft 16 and spring 34. The third interior portion 42 having a narrow slot shape to receive the mixing surface 18 extends across the diameter of the dispensing surface 13 and into the plunger body 12. In the retracted position shown in FIGS. 1 and 2, the edges 30 of the mixing surface 18 touch the interior of the syringe barrel 24. Shown in FIGS. 1 and 4, the third interior portion 42 may optionally include a plunger seal 43 on the dispensing surface 13 to prevent the substance 25 from entering the third interior portion 42 when the mixing surface 18 is retracted. The plunger seal 43 may include two rubber strips that touch or overlap to create an obstruction sufficiently rigid to allow the mixing surface 18 to pass through but prevent the substance 25 from such passing. Further, although the shaft 16 is axially moveable throughout the plunger body 12, the spring 34 is held against the shoulder 44 formed at the interface of the second interior portion 40 and the third interior portion 42.

Figure 5:
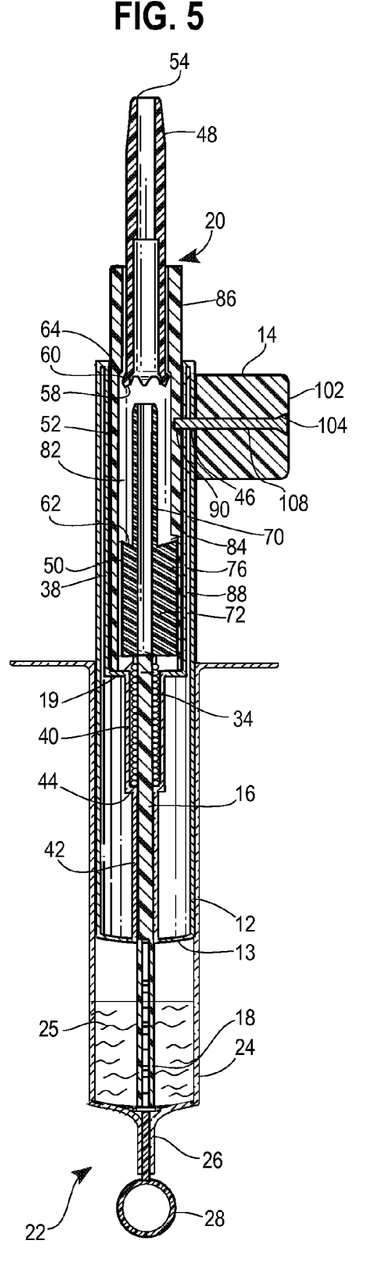
FIG. 5 is a cross sectional view of Section 5-5 of FIG. 4.
Figure 7:
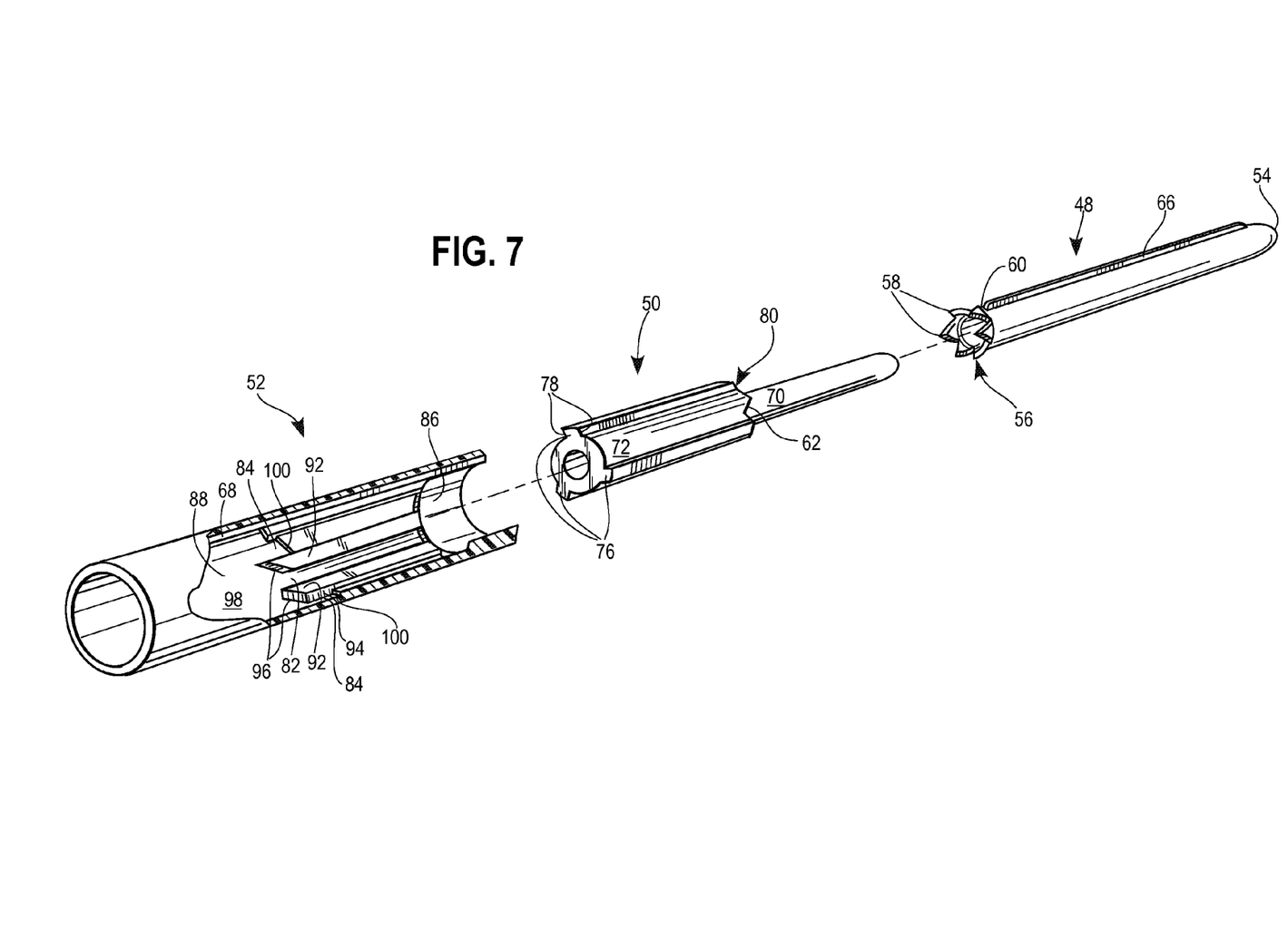
FIG. 7 is an exploded view of the retractor locking assembly.

Referring to FIG. 7, the retractor locking assembly 20 includes a retractor top 48 and a retractor bottom 50 which are coaxially assembled within a retractor housing 52. The retractor top 48 is cylindrical and has a first top end 54 and a second top end 56. The first top end 54 provides a surface for actuation of the retractor locking assembly 20, whereby pressure applied to the first top end 54 relative to the housing 52 causes the mixing surface 18 to move between the extended and retracted positions. The second top end 56 has a first toothed surface 58, wherein each tooth arcs outwardly from the adjacent surface and extends toward the retractor bottom 50 to form a shoulder 60. The first toothed surface 58 engages with a corresponding second toothed surface 62 of the retractor bottom 50. As seen in FIGS. 2 and 5, the retractor top 48 is slidably disposed within the retractor housing 52 such that the shoulder 60 engages a stop limit 64 as an abutment limiting outward movement of the retractor top 48 from the retractor housing 52. Further, the exterior of the retractor top 48 is formed with a longitudinal guide rib 66 to mate with a guide groove 68 formed on the interior of the retractor housing 52 as shown in FIG. 7.

The retractor bottom 50 having a first bottom portion 70 and a second bottom portion 72 is positioned such that the first bottom portion 70 is received by the second top end 56. The second toothed surface 62 on the second bottom portion 72 extends toward the retractor top 48 and correspondingly mates with the toothed surface 58 of the second top end 56. The tips of the toothed surfaces 58, 62 are slightly offset relative to one another to enable rotation of the retractor bottom 50, described in more detail below.

Figure 3:
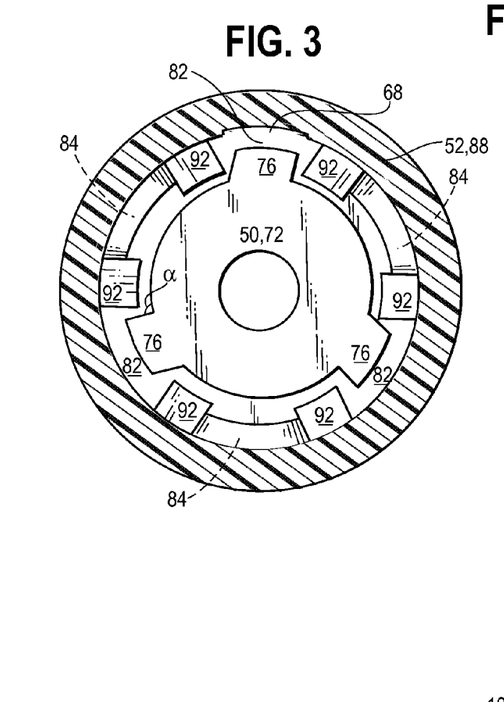
FIG. 3 is a cross sectional view of Section 3-3 of FIG. 1.
Figure 6:
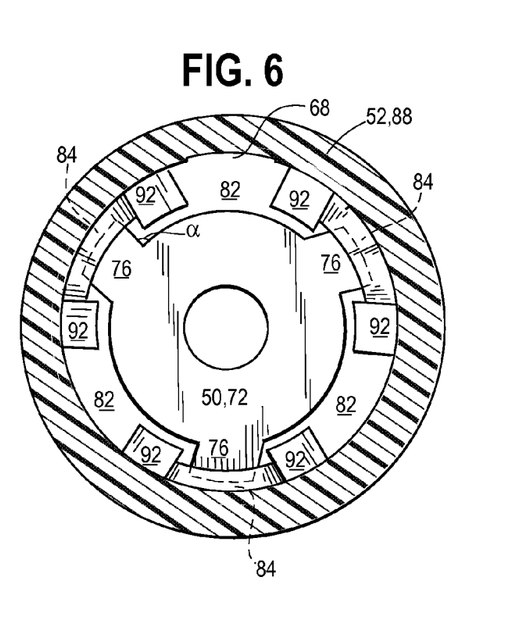
FIG. 6 is a cross sectional view of Section 6-6 of FIG. 4.

In order to guide the sliding movement of the retractor bottom 32 within the retractor housing 52, three longitudinal bottom ribs 76 spaced equidistantly around the exterior of the second bottom portion 72 engage with a plurality of corresponding first and second cam grooves 82, 84 formed on the interior of the retractor housing 52, as seen in FIGS. 3, 6, and 7. Each bottom rib 76 has a bottom rib end 80 and two side surfaces 78 which project from the second bottom portion 72 at an angle α. The first bottom rib end 80 is angled so as to be coplanar with the adjacent second toothed surface 62.

The retractor housing 52 has a hollow interior with a first housing portion 86 and a second housing portion 88 which form the stop limit 64. The second housing portion 86 includes a housing aperture 90 (seen in FIGS. 2 and 5) and six longitudinal housing ribs 92, each of which extends from the stop limit 64 and has two housing rib side surfaces 94 and a slanted housing rib end 96. The housing ribs 92 annularly form three first cam grooves 82 and three second cam grooves 84 on an interior 98 of the second housing portion 86. Shown FIGS. 3 and 6, the first and second cam grooves 82, 84 are arranged in an alternating pattern such that the bottom ribs 70 engage either the first cam grooves 82 or the second cam grooves 84 when assembled. When the device is in the retracted position seen in FIG. 3, the bottom ribs 76 of the retractor bottom 50 mate with the first cam grooves 82 of the retractor housing 52. Conversely, when the device is in the extended position as shown in FIG. 6, the bottom ribs 76 of the retractor bottom 50 mate with the second cam grooves 82 of the retractor housing 52.

As seen in FIG. 7, each first and second cam groove 82, 84 has an interior surface level with the adjacent interior 98 and is bounded by two side walls 94 of two adjacent housing ribs 92. The first and second cam grooves 82, 84 differ in that the upper boundary of each first cam groove 82 is the stop limit 64 whereas the upper boundary of each second cam groove 84 is a slanted raised surface end 100 that protrudes from the adjacent interior 98. The upper boundaries are spaced apart at a length equal to or greater than the length of the edges 30 of the mixing surface 18 so that the mixing surface 18 is fully withdrawn when the bottom ribs 70 are in the first cam grooves 82 in the retracted position as shown in FIG. 2 and fully projects from the dispensing surface 13 of the plunger 12 when the bottom ribs 70 are in the second cam grooves 84 in the extended position as shown in FIG. 5.

When the bottom ribs 76 are in the first cam grooves 82, the shoulder 60 of the retractor top 48 abuts the stop limit 64 of the retractor housing 52, and the retractor bottom 50 mates with the retractor top 48 at the first and second toothed surfaces 58, 62 under the influence of the spring 34 as shown in FIGS. 1-3. FIGS. 4-6 demonstrate that when the bottom ribs 76 are in the second cam grooves 84, the bottom rib ends 80 of the bottom ribs 76 sit against the raised surface end 100 of the second cam grooves 84 under the influence of the spring 34, and the retractor top 48 is moveable between the mating of the first and second toothed surfaces 58, 62 adjacent the raised surface ends 100 and the abutting of the shoulder 60 of the retractor top 48 against the stop limit 64. The guide groove 68 for receiving the guide rib 66 of the retractor top 48 is formed on the interior of the first and second housing portions 86, 88 within a first cam groove 82 as seen in FIGS. 3, 6, and 7.

For the purpose of describing operation of the retractor assembly, it is assumed that the retractor locking assembly 20 is initially in the retracted position. Shown in FIGS. 1-3, the bottom ribs 76 of the retractor bottom 50 are positioned in the first cam grooves 82 of the retractor housing 52 as the spring 34 urges the retractor bottom 50 toward the retractor top 48. Pressure applied to the first top end 54 of the retractor top 48 causes retractor top 48 and bottom 50 to slide relative to the retractor housing 52. The bottom ribs 76 slide out of the first cam grooves 82 and into the adjacent interior 98 of the second housing portion 88 against the bias of the spring 34. As the pressure is removed from the first top end 54 of the retractor top 48, the spring 34 urges the second toothed surface 62 on the retractor bottom 50 to engage with the adjacent housing rib 92 of the retractor housing 52 due to the slight offset between the tips of the first and second toothed surfaces 58, 62. The bottom ribs 76, acting as a cam, rotate and track the adjacent housing rib end 96 of the adjacent housing rib 92 and raised surface end 100 of the second cam groove 84. The offset and teeth of the first and second toothed surfaces 58, 62 and the angles and slants of the side edges 78 and bottom rib ends 80 of the bottom ribs 76, the housing rib ends 96 of the housing ribs 92, and the raised surface ends 100 of the second cam grooves 84 interact under the influence of the spring 34 to effectuate rotation of the retractor bottom 50 relative to the retractor housing 52. With the bottom ribs 76 in the second cam grooves 84, the retractor locking assembly 20 holds the mixing surface 18 in the extended position as shown in FIGS. 4-6. During operation, the guide rib 66 and groove 68 of the retractor top 48 and housing 52, respectively, prevent the retractor top 48 from rotating relative to the retractor housing 52. To move the mixing surface 18 from the extended position to the retracted position, actuation of the retractor locking assembly 20 causes the bottom ribs 76 to move out of the second cam grooves 84 and into the first cam grooves 82 in the manner described above.

In the preferred embodiment shown in FIGS. 1-6, the off center mass 14 secured to the plunger body 12 enables the device 10 to rotate relative to the syringe 22 when the syringe 22 and device 10 are positioned upright and moved in a circular motion. The off center mass 14 having a cylindrical shape with a solid body includes a planar end 102 with a central mass aperture 104 and an open end 106. The open end 106 is shaped to correspond to the exterior of the plunger body 12 as shown in FIGS. 1 and 4. The plunger body 12, the retractor housing 52, and the off center mass 14 are positioned to align the plunger aperture 46, the housing aperture 90, and the mass aperture 104. Shown in FIGS. 2 and 5, a bolt 108 is inserted through the apertures 46, 90, 104 to secure the plunger body 12, the retractor housing 52, and the off center mass 14 relative to each other. Other fastening means may be used as well.

Figures 8, 9:
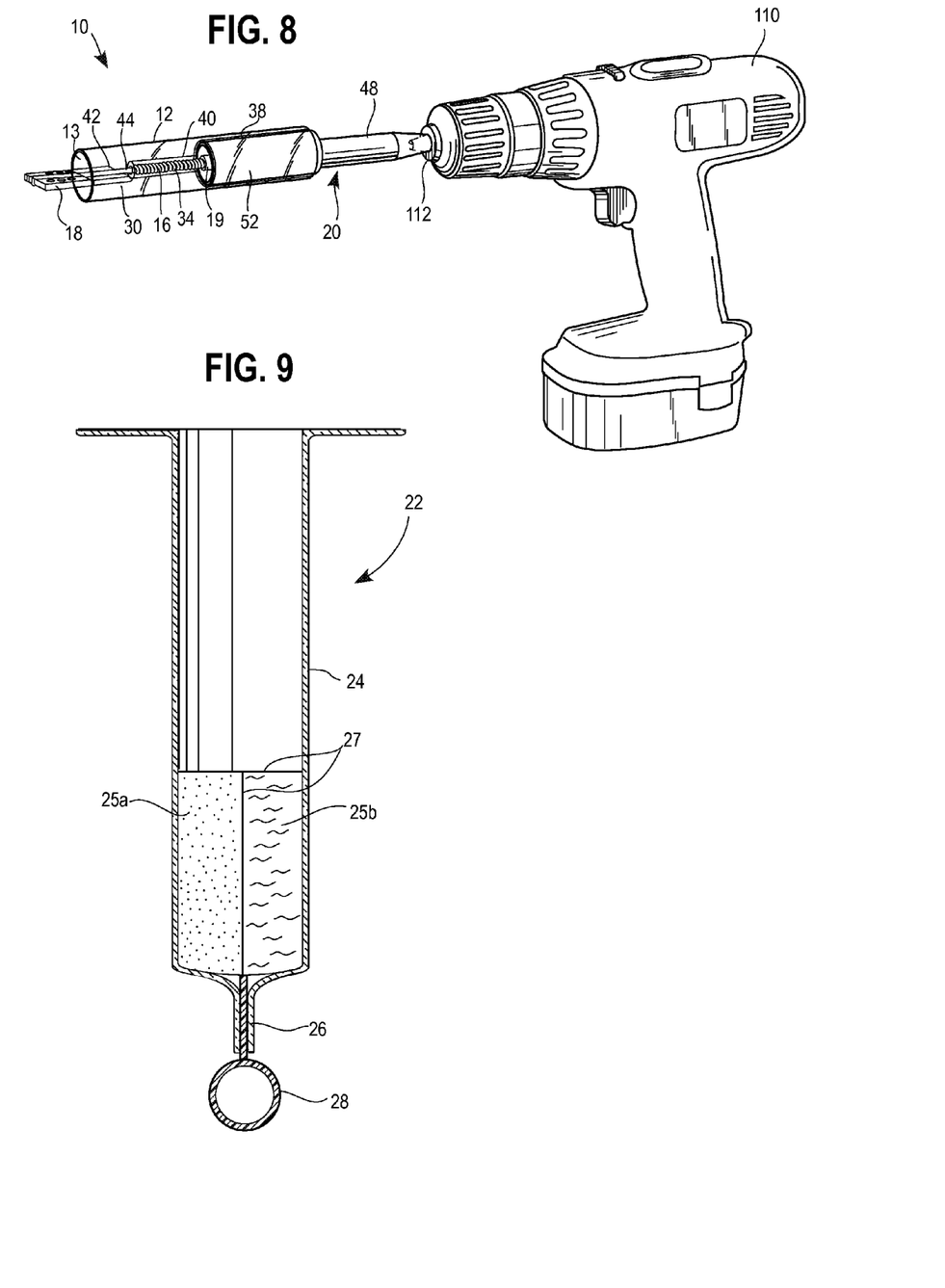
FIG. 8 is a perspective view of an alternative embodiment of the device in the extended position.
FIG. 9 is a cross sectional view of the syringe barrel preloaded with the components of the biomaterial.

In an alternative embodiment shown in FIG. 8, the device may be attached to a power tool 110 to enable a user to grasp the syringe 22 and rotate the device 10 upon powering of the tool 110. The power tool 110 includes a standard chuck 112 in which an interface that is either the retractor top 48 shaped to be securely held by the chuck 112 or is a structure (not shown) in the first top end 54 that enables a device (not shown) that is fixed in the chuck 112 to be attached to the top end 54. The shape of the retractor top 48 may be altered to accommodate different chuck designs. While a power hand tool 110 is shown in FIG. 8, other power tools such as a custom made hand drill or the like may be used.

Operation of the device will now be described. With the cap 28 positioned in the nozzle 26, a substance 25 is loaded into the barrel 24. The mixing surface 18 is locked in the extended position as shown in FIGS. 4-6, and the mixing surface 18 and dispensing surface 13 of the plunger body 12 are inserted into the barrel 24. The user then places the syringe 22 and device 10 in an upright position with retractor locking assembly 20 at the highest point, grasps the syringe 22, and moves the syringe 22 in a circular motion so that the off center mass 14 causes the device 10 to rotate relative to the syringe 22. Once the substance 25 is sufficiently mixed, the user stops the circular motion and the device 10 comes to a rest within the syringe 22. The user then actuates the retractor locking assembly 20 by pressing and releasing the first top end 54 of the retractor top 48 relative to the retractor housing 52 to cause the mixing surface 18 to retract into the plunger body 12. Once pressure is removed from the first top end 54, the mixing surface 18 is locked in the retracted position as shown in FIGS. 1-3. The user then removes the cap 28 from the nozzle 26 of the syringe 22, positions the nozzle 26 over the area onto which the mixed substance 25 is to be applied, and applies pressure to the plunger body 12 in order to force the dispensing surface 13 to act on and dispense the substance 25.

Alternatively, the syringe 22 may be preloaded with one or more components of the substance 25. FIG. 9 shows the syringe 22 preloaded with a powdered component 25a and a liquid component 25b separated by a component seal 27. The syringe barrel 24 may otherwise be preloaded with a single component 25a or 25b enclosed in the component seal 27, and the user may add the other components or additives. The component seal 27 may be made of a film material such as an elastomer. Examples of suitable elastomers which can be used, without limitation, are polyacrylate (ACM), ethylene acrylate (AEM), butyl rubber (IIR), polychloroprene rubber (CR), ethylene propylene rubber (EPM, EPR, EPDM), fluorosilicone (FVMQ), acrylonitrile-butadiene (NBR), hydrogenated nitrile (HNBR, HSN), polyurethane (AU, EU), silicone rubber (VMQ, PVMQ), fluorocarbon (FKM, FPM), tetrafluoroethylene-propylene (AFLAS™), high performance fluoroestaomer (Hifluor™), perfluoroelastomer (Parofluor), and perfluoroelastomer (Parofluor Ultra). The components 25a, 25b may be packaged under vacuum, nitrogen, or dry air to preserve the shelf life. In this embodiment, the mixing surface 18 is locked in the retracted position and inserted into the syringe 22. Securely holding the syringe 22 and device 10, the user then actuates the retractor locking assembly 20. The force of the projection of the mixing surface 18 from the dispensing surface 13 of the plunger body 12 breaks the component seal 27 and allows the components 25a, 25b to combine. The user then mixes and applies the substance 25 as described above.

Figure 10:
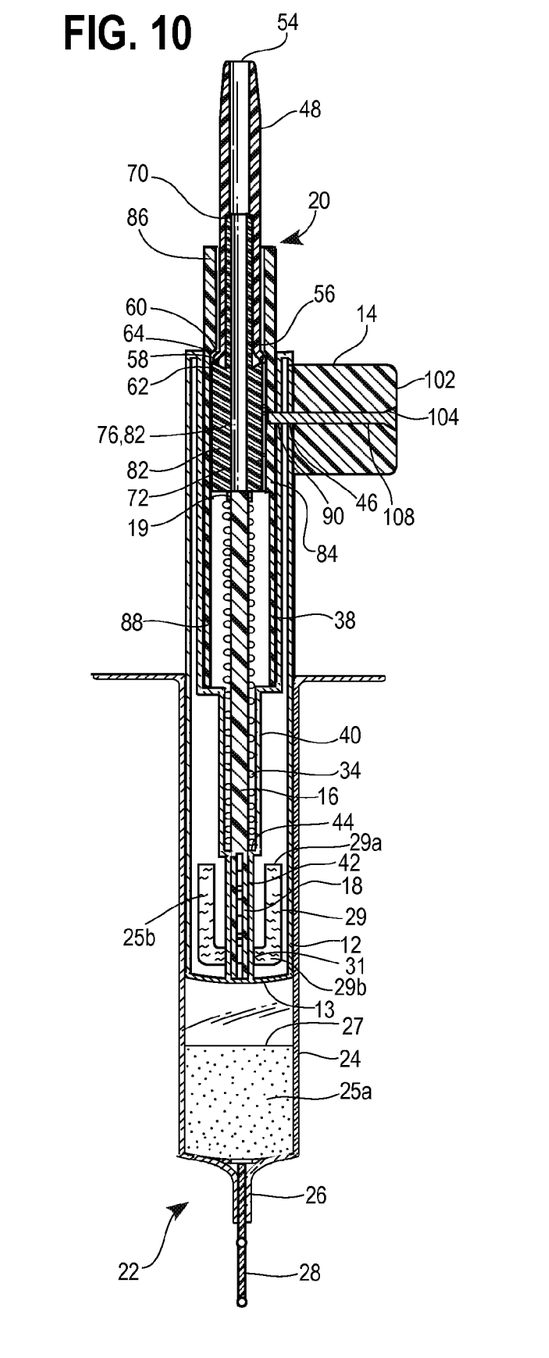
FIG. 10 is a cross sectional view of an alternative embodiment of the syringe barrel preloaded with the components of the biomaterial.

FIG. 10 shows another embodiment of the preloaded syringe 22 where the liquid component 25b is stored in two cavities 29 within the plunger body 12. The powdered component 25a may be enclosed by the component seal 27 in the barrel 24 of the syringe 22. Each longitudinal cavity 29 having a top end 29a and a bottom end 29b formed in the plunger body 12 is vertically oriented with a horizontal connection to the third interior portion 42 at the bottom end 29b. The vertical component of each cavity 29 is centrally located within the solid portion of the plunger body 12 on opposite sides of the third interior portion 42. When the mixing surface 18 is in the retracted position, the mixing surface 18 blocks the openings of the two cavities 29 and prevents the liquid component 25b from flowing out of the cavities 29. When the mixing surface 18 is moved to the extended position, the liquid component 25b is released from each cavity 29 and combines with the powdered component 25a to form substance 25. Optionally, a second component seal 31 positioned at each bottom end 29b and broken by movement of the mixing surface 18 into the extended position may further prevent leakage of the liquid component 25b from the cavities 29.

It is further envisioned that the device disclosed herein may be packaged into a kit that may include a syringe or similar vessel. The syringe 22 may be preloaded with one or more components of the bone cement enclosed by a seal. Further, if additives are used, they may be included within this syringe or in a separate vial. The kit may include mixing bowls, stirring sticks, spatulas, syringes, and/or any other desirable component for application.

The disclosure has been presented in an illustrative manner in order to enable a person of ordinary skill in the art to make and use the disclosure, and the terminology used is intended to be in the nature of description rather than of limitation. It is understood that the disclosure may be practiced in ways other than as specifically disclosed, and that all modifications, equivalents, and variations of the present disclosure, which are possible in light of the above teachings and ascertainable to a person of ordinary skill in the art, are specifically included within the scope of the impending claims. All patents, patent publications, and other references cited herein are incorporated herein by reference.

I claim:

1. A method for mixing and applying a substance comprising the steps of:
    positioning a mixing surface in a retracted position wherein the mixing surface is retracted into a plunger body having a dispensing surface;
    positioning the dispensing surface of the plunger body within a vessel, wherein the vessel is preloaded with at least one component of the substance enclosed by a seal;
    positioning the mixing surface in the extended position wherein the mixing surface projects from the plunger body;
    moving the vessel in a circular motion such that an offset mass connected to the plunger body effectuates rotation of the mixing surface with respect to the vessel;
    positioning the mixing surface in a retracted position wherein the mixing surface is retracted into the plunger body; and
    forcing the dispensing surface to act on and dispense the substance.

* * * * *